(12) United States Patent (10) Patent No.: US 12,042,944 B2
Waterson (45) Date of Patent: Jul. 23, 2024

(54) ROBOTIC SURGICAL SYSTEM WITH GRAPHICAL USER INTERFACE

(71) Applicant: DePuy Ireland Unlimited Company, Ringaskiddy (IE)

(72) Inventor: Heather Rae Waterson, Warsaw, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 1092 days.

(21) Appl. No.: 16/834,613

(22) Filed: Mar. 30, 2020

(65) Prior Publication Data

US 2021/0299877 A1   Sep. 30, 2021

(51) Int. Cl.
*B25J 9/16* (2006.01)
*A61B 34/00* (2016.01)
(Continued)

(52) U.S. Cl.
CPC ............ *B25J 9/1697* (2013.01); *A61B 34/20* (2016.02); *A61B 34/25* (2016.02); *A61B 34/30* (2016.02);
(Continued)

(58) Field of Classification Search
CPC ......... B25J 9/1697; B25J 13/06; A61B 34/20; A61B 34/25; A61B 34/30;
(Continued)

(56) References Cited

U.S. PATENT DOCUMENTS 6,450,978 B1   9/2002   Brosseau et al.
6,470,207 B1   10/2002   Simon et al.
(Continued)

FOREIGN PATENT DOCUMENTS

AU   2005237479 B2   11/2005
AU   2007351804 B2   10/2008
(Continued)

OTHER PUBLICATIONS

Brainlab AG, Knee 3 Surgical Technique, Jun. 2015, REV. 1, https://www.brainlab.com/wp-content/uploads/2016/12/Knee3-Surgical-Technique.pdf.
(Continued)

*Primary Examiner* — Harry Y Oh
(74) *Attorney, Agent, or Firm* — Etan S. Chatlynne; Calderon Safran & Wright P.C.

(57) ABSTRACT

A robotic surgical system comprising a robotic surgical apparatus and a graphical user interface (GUI) system may be used to assist a user in performing a surgical procedure. The GUI system may comprise a spatial-data acquisition device, a data acquisition device having a pointer with a tip, a display, and an operating console including a non-transitory storage medium and a processor. The robotic surgical apparatus, the spatial-data acquisition device, the display, and the non-transitory storage medium may be connected to the processor. The processor may be configured to receive as inputs spatial data from the spatial-data acquisition device and provide as outputs to the display a set of indications for positioning the robotic surgical apparatus at the anatomical target. The processor may also be configured to provide as outputs to the display a set of indications for confirming the reference surface location of the anatomical structure.

15 Claims, 8 Drawing Sheets

(51) Int. Cl.
*A61B 34/20* (2016.01)
*A61B 34/30* (2016.01)
*B25J 13/06* (2006.01)
*G06F 3/0481* (2022.01)
*G06T 7/70* (2017.01)
*H04N 5/33* (2023.01)

(52) U.S. Cl.
CPC .......... *B25J 13/06* (2013.01); *G06F 3/0481* (2013.01); *G06T 7/70* (2017.01); *A61B 2034/2057* (2016.02); *A61B 2034/252* (2016.02); *A61B 2034/254* (2016.02); *G06T 2207/10048* (2013.01); *G06T 2207/30004* (2013.01); *H04N 5/33* (2013.01)

(58) Field of Classification Search
CPC ...... A61B 2034/2057; A61B 2034/252; A61B 2034/254; A61B 2034/2055; A61B 2034/2068; G06F 3/0481; G06T 7/70; G06T 2207/10048; G06T 2207/30004; H04N 5/33
See application file for complete search history.

(56) References Cited

U.S. PATENT DOCUMENTS

| | | |
|---|---|---|
| 6,711,432 B1 | 3/2004 | Krause et al. |
| 6,990,220 B2 | 1/2006 | Ellis et al. |
| 7,167,738 B2 | 1/2007 | Schweikard et al. |
| 7,203,277 B2 | 4/2007 | Birkenbach et al. |
| 7,594,933 B2 * | 9/2009 | Kammerzell ......... A61B 34/20 623/22.15 |
| 7,636,595 B2 | 12/2009 | Marquart et al. |
| 7,678,147 B2 | 3/2010 | Clifford et al. |
| 7,699,793 B2 | 4/2010 | Götte et al. |
| 7,715,602 B2 | 5/2010 | Richard |
| 7,831,292 B2 * | 11/2010 | Quaid .................. A61B 34/37 345/157 |
| 7,835,778 B2 | 11/2010 | Foley et al. |
| 7,905,924 B2 | 3/2011 | White |
| 7,974,677 B2 | 7/2011 | Mire et al. |
| 8,078,440 B2 | 12/2011 | Otto et al. |
| 8,126,533 B2 | 2/2012 | Lavallee |
| 8,295,909 B2 | 10/2012 | Goldbach |
| 8,323,290 B2 | 12/2012 | Metzger et al. |
| 8,382,765 B2 | 2/2013 | Axelson et al. |
| 8,571,637 B2 | 10/2013 | Sheffer et al. |
| 8,706,197 B2 | 4/2014 | Henning et al. |
| 8,888,782 B2 | 11/2014 | Smith et al. |
| 8,894,714 B2 | 11/2014 | Makower et al. |
| 9,498,231 B2 | 11/2016 | Haider et al. |
| 9,852,268 B2 | 12/2017 | Gotte |
| 10,105,149 B2 | 10/2018 | Haider et al. |
| 10,191,302 B2 | 1/2019 | Bailey et al. |
| 10,452,238 B2 | 10/2019 | Nikou et al. |
| 2002/0198451 A1 | 12/2002 | Carson |
| 2003/0069591 A1 | 4/2003 | Carson et al. |
| 2003/0176783 A1 | 9/2003 | Hu |
| 2007/0016008 A1 | 1/2007 | Schoenefeld |
| 2007/0270680 A1 * | 11/2007 | Sheffer ................. A61B 34/20 600/407 |
| 2009/0254098 A1 * | 10/2009 | Christian ............... A61B 34/10 606/130 |
| 2009/0264737 A1 | 10/2009 | Haechler et al. |
| 2010/0153081 A1 | 6/2010 | Bellettre et al. |
| 2014/0324403 A1 | 10/2014 | Gotte |
| 2016/0331474 A1 | 11/2016 | Lacal et al. |
| 2019/0290370 A1 | 9/2019 | Brummund et al. |

FOREIGN PATENT DOCUMENTS

| | | |
|---|---|---|
| CA | 2 706 356 C | 3/2017 |
| CA | 2 715 315 C | 4/2017 |
| CN | 102985025 A | 3/2013 |
| DE | 100 31 887 A1 | 1/2002 |
| DE | 102 15 808 B4 | 2/2005 |
| DE | 600 32 475 T2 | 9/2007 |
| DE | 10 2016 202 578 A1 | 8/2017 |
| EP | 1 226 788 A1 | 7/2002 |
| EP | 1 153 572 B1 | 8/2002 |
| EP | 1 832 230 B1 | 8/2010 |
| EP | 1 836 978 B1 | 7/2011 |
| EP | 2 044 884 B1 | 12/2015 |
| EP | 2 787 887 B1 | 2/2016 |
| EP | 3 549 553 A3 | 1/2020 |
| ES | 2 216 789 T3 | 11/2004 |
| ES | 2 228 043 T3 | 4/2005 |
| FR | 2 895 267 A1 | 6/2007 |
| JP | 3990719 B2 | 10/2007 |
| JP | 43720000 B2 | 11/2009 |
| KR | 10-0747138 B1 | 8/2007 |
| KR | 10-1660904 B1 | 9/2016 |
| WO | 2004/017836 A2 | 3/2004 |
| WO | 2004/032780 A1 | 4/2004 |
| WO | 2006/092600 A1 | 9/2006 |
| WO | 2007/067150 A1 | 6/2007 |
| WO | 2007/106172 A1 | 9/2007 |
| WO | 2013/052187 A3 | 4/2013 |
| WO | 2013/083297 A1 | 6/2013 |
| WO | 2013/177675 A1 | 12/2013 |
| WO | 2017/179075 A1 | 10/2017 |
| WO | 2018/045086 A1 | 3/2018 |
| WO | 2019/139935 A1 | 7/2019 |

OTHER PUBLICATIONS

PCT Invitation to Pay Additional Fees and Where Applicable, Protest Fee and Annex to Form PCT/ISA/206 Communication related to the Results of the Partial International Search Report for PCT/EP2021/05817515 dated Jul. 6, 2021, 15 Pages.

PCT Notification of Transmittal of the International Search Report and the Written Opinion of the International Searching Authority, or the Declaration, International Application No. PCT/EP2021/058175 Dated Oct. 14, 2021, 22 Pages.

* cited by examiner

ROBOTIC SURGICAL SYSTEM WITH GRAPHICAL USER INTERFACE

FIELD

The subject matter disclosed herein relates to equipment and techniques for performing robotic surgery.

BACKGROUND

Automated or remote-controlled surgical devices, including robots, are used in conducting various surgical procedures to perform functions that may be difficult for a human surgeon to perform. For example, in minimally invasive procedures where surgical instruments are inserted into body cavities through small incisions cut in a subject's tissue, e.g., laparoscopic procedures, automated or remote-controlled devices, particularly those associated with a visualization system, have been used to facilitate manipulation of tissues in the cavity.

SUMMARY OF THE DISCLOSURE

A robotic surgical system comprising a robotic surgical apparatus and a graphical user interface (GUI) system may be used to assist a user, e.g., healthcare professional, who is performing a surgical procedure. The GUI system may comprise a spatial-data acquisition device, a data acquisition device having a pointer with a tip, a display, and an operating console including a non-transitory storage medium and a processor. The robotic surgical apparatus, the spatial-data acquisition device, the display, and the non-transitory storage medium may be connected to the processor. The processor may be configured to receive as inputs spatial data from the spatial-data acquisition device and provide as outputs to the display a set of indications for positioning the robotic surgical apparatus at the anatomical target. The set of indications for positioning the robotic surgical apparatus at an anatomical target may comprise a first instruction image reflecting the robotic surgical apparatus positioned at a first location, a second instruction image reflecting the robotic surgical apparatus positioned at a second location that is closer to the anatomical target than the first location, and a third instruction image reflecting the robotic surgical apparatus at the anatomical target. These instruction images may also include directional indications of directions from the apparatus's location toward the anatomical target.

Additionally or alternatively, the processor may be configured to provide as outputs to the display a set of indications for confirming the reference surface location of the anatomical structure. The set of indications for confirming the reference surface location of an anatomical structure may comprise a review image reflecting the anatomical structure, a reference point on the review image representing the reference surface location on the anatomical structure, a moveable point on the review image representing the tip of the data acquisition device, and a message box for indicating a distance between the reference surface location and the location of the tip of the data acquisition device.

As used herein, the term "navigation device" refers to any device, structure, component, assembly, apparatus, or system that may be associated with a physical object for the purpose of enabling a prompt detection of the location of the physical object by a navigation system (e.g., visual imaging systems, thermographic imaging systems, electromagnetic imaging systems) or a larger system, such as the robotic surgical system described herein, that comprises an imaging system (and in the specific disclosed embodiments comprises a visual imaging system including a camera, a processor, and a storage medium). Examples of navigation devices may include, but are not limited to, position sensors, antennas, navigation arrays, gyroscopes, and accelerometers.

As used herein, the term "image" or "images" encompasses images including, but not limited to, photographic images taken by a camera or a video camera, thermographic images (e.g., an image based on infrared energy of physical structures) taken by a thermographic camera (e.g., an infrared camera that is operable to detect and measure infrared energy from physical structures), or any other representation of physical structures, including two-dimensional or three-dimensional spatial information regarding the physical structures based on data collected by non-photographic devices (e.g., electromagnetic position sensors or mapping sensors), as well as electronic media (e.g., digital photographs and computer-aided designs) that may be displayed on an electronic display (e.g., computer monitor, laptop screen, tablet, electronic paper, e-reading device) or otherwise provided or printed in a manner involving non-electronic media (e.g., paper or physical prototype, such as 3D printing).

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values+10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Robotic surgical systems may be used to assist healthcare professionals to conduct medical procedures. Applicant has devised various improvements to this technology and presents examples of these improvements as the subject matter disclosed herein. These examples are directed to orthopedic surgical procedures, particular concerning the knee. However, the techniques described are applicable to other procedures that employ a robotic surgical apparatus, including non-orthopedic procedures.

Figure 1:
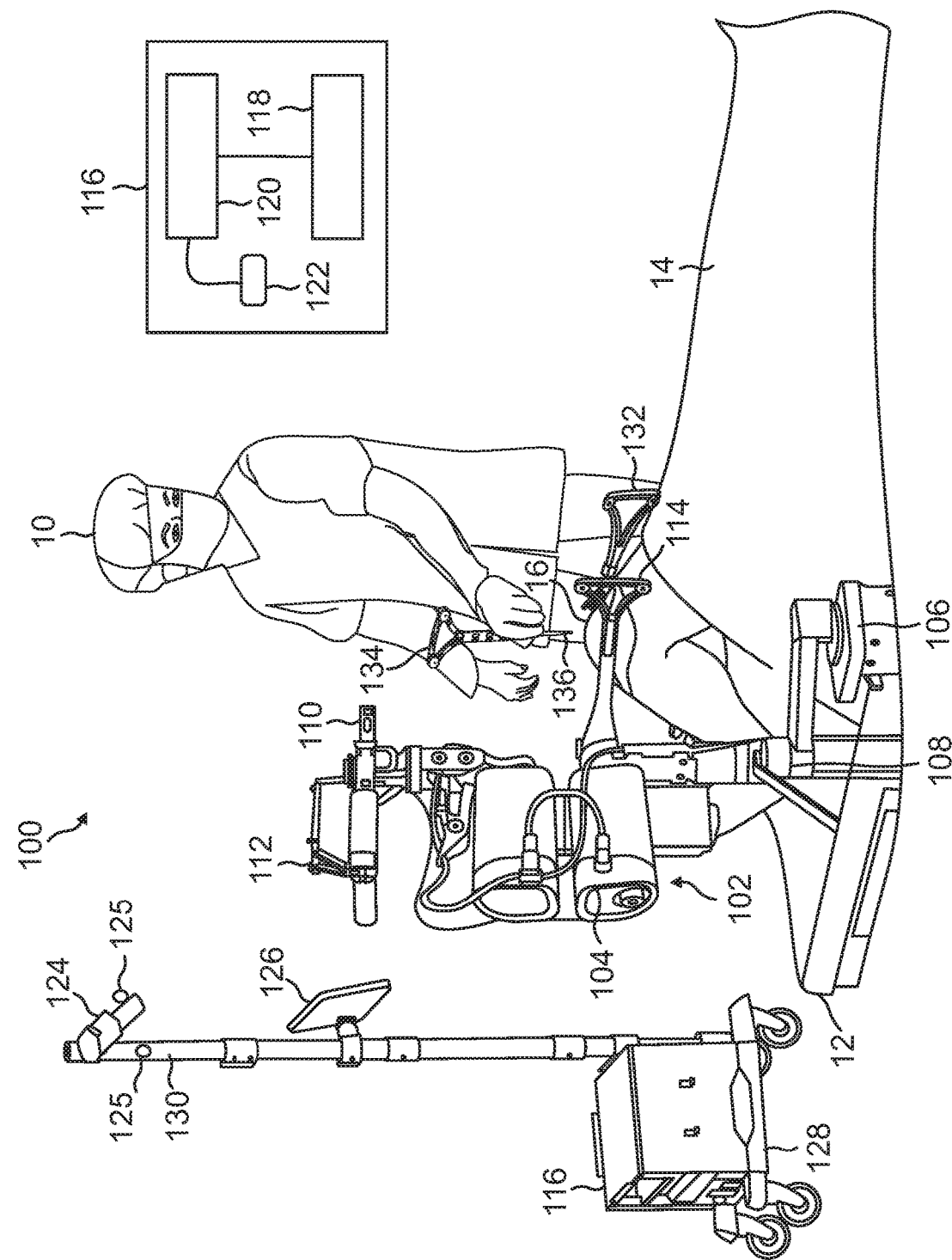
FIG. 1 depicts a scene from an operating room in which a surgeon is performing a surgical procedure using a robotic surgical system including a robotic surgical apparatus and a graphical user interface (GUI) system comprising a display, a spatial-data acquisition device, and an operating console, with a block diagram of the operating console therebeside.

FIG. 1 reflects a scene from an operating room in which an orthopedic procedure is being performed by a healthcare professional or surgeon 10 on a subject laying on a surgical bed 12 and covered by surgical blanket 14. In this scene, the subject's knee joint 16 has been exposed for a knee-replacement surgery that includes steps of resecting bone and subsequently attaching prosthetics to the resected bone. That is, the distal end of the subject's femur and the proximal end of the subject's tibia have been exposed by incising the subject's skin and other tissues over the knee and displacing the subject's patella. However, no resections have yet been performed in this scene. Rather, in this, scene surgeon 10 is preparing to perform these resections with the assistance of robotic surgical system 100. Such preparation requires various procedures, of which two exemplary procedures form the focus of the present application.

Robotic surgical system 100 includes a robotic surgical apparatus 102. Robotic surgical apparatus 102 includes a robot body 104 and a fixation mechanism (e.g., clamp) 106 that may be used to attach body 104 to another structure, e.g., a fixed structure, such as bed 12. A mechanism 108 comprising arms and joints may be used to adjust and then set the position of body 104 relative to clamp 106. Apparatus 102 also includes an end effector 110 (e.g., saw, burr, cannula, drill, retractor) and an end-effector navigation device 112 attached thereto. A robot navigation device 114 is attached to body 104.

Robotic surgical system 100 also comprises one or more anatomy navigation arrays. The anatomy navigation array or arrays may be attached to bones. In the scene of FIG. 1, a femur navigation array 132 is reflected. A tibial navigation array may additionally be provided.

Robotic surgical system 100 also includes a pointer navigation device 134, which the surgeon may use to acquire surface data of anatomical structures, such as the proximal portion of the tibia and the distal portion of the femur of knee 14. Accordingly, pointer navigation device 134 is also referred to herein as a "data acquisition device." As seen in FIG. 1, data acquisition device 134 includes a pointer 136 having a tip. Surgeon 10 may acquire surface data of anatomical structures (e.g., tibia and femur) by contacting the tip of pointer 136 to the surface of the anatomical structure.

Robotic surgical system 100 also comprises an operating console 116, which, as reflected in the schematic representation thereof in FIG. 1, includes a non-transitory storage medium 118, a processor 120, and a communication module 122 for receiving and transmitting signals between processor 120 and other components of system 100, such as a spatial-data acquisition device (e.g., camera 124), navigation devices (e.g. pointer navigation device 134), display 126, and end effector 110. Furthermore, mechanism 108 may be motorized such that it may also be controlled by processor 120 to position robot body 104. Communication module may be for wired communication, wireless communication, or both, e.g., Ethernet, Wi-Fi, Bluetooth, etc. Non-transitory storage medium 134 may be, e.g., random access memory (RAM), a hard-disk drive, or flash memory or any other non-transitory storage medium which can store software or logic that processor 120 may execute to operate robotic surgical system 100 and process data, such as images captured by camera 108. As explained below, spatial data may be processed by processor 120 to determine instructions that may assist the surgeon in using the robotic surgical system. Further processor 120 may provide graphical representations of these instructions (which may be stored in storage medium 134 such that processor 120 may select them instead of create them) to display 126 where they may be displayed to the surgeon.

Robotic surgical system 100 also comprises spatial-data acquisition device (e.g., camera 124) and display 126. Operating console 116, spatial-data acquisition device (e.g., camera 124), and display 126 may all be physically connected to each other, e.g., on cart 128 as seen in FIG. 1, with operating console disposed on the cart and display 126 connected to a support 130 of the cart, preferably at a comfortable viewing position for the surgeon. Where spatial-data acquisition device is an imaging device such as camera 124, it may be disposed elsewhere on support 130 to collect spatial data concerning or images of a procedural field, which should comprise at least apparatus 102 and knee 16. Of course, other arrangements of console 116, spatial-data acquisition device, and display 126 may be employed, e.g., each may be provided on separate carts.

Camera 124 may comprise one or more cameras, e.g., thermographic cameras, such as infrared cameras. Camera 124 may further comprise sources of infrared energy 125, such as infrared diodes or LEDs. Alternatively or additionally, such sources of infrared energy 125 may be provided separately from cameras 124, e.g., elsewhere on support 130. Infrared energy provided from one or more sources 125 may be reflected by structures in the procedural field, such as at least one of the various navigation devices described herein (i.e., 112, 114, 132, and 134). Camera 124 receives and records the reflected infrared energy as data, e.g., one or more infrared images, which thus comprises spatial data. Camera 124 then provides these data as inputs to processor 120 either directly or indirectly via an initial delivery of the data to storage medium 118 such that processor 120 may subsequently retrieve the data from storage medium 118.

Alternatively or additionally, robotic surgical system 100 may include a navigation or mapping system for determining positions of navigation devices 112, 114, 132, and 134 without use of visual or thermographic images. As such, the spatial-data acquisition device need not be a camera. Rather, other types of spatial-data acquisition devices, e.g., position sensors, may be employed. For example, the position sensors may be a set of three non-concentric coils that, when disposed in an externally applied magnetic field, have currents induced therethrough. The currents in the three coils of any such three-coil set comprise spatial data and may be provided as inputs to the processor or to storage medium 118 such that processor 120 may subsequently retrieve the data from storage medium 118. The processor may analyze the data to determine three degrees of position and three degrees of orientation for any such three-coil set in each navigation array. Such analysis and determination may be performed continuously. Furthermore, the navigation devices may include other types of sensors, e.g., pressure sensors. For example, a pressure sensor may be provided on the tip of pointer 136 of pointer navigation device 134, such that a threshold pressure being registered by the pressure sensor could be provided as data input to processor 120 that processor 120 may interpret as, e.g., a surface location of an anatomical structure (e.g., bone), an instruction to begin processing spatial data from any three-coil sets in pointer navigation device 120, or both.

Display 126 may be used to display various screens comprising representations of instructions for using robotic surgical system 100. These instructions assist the surgeon in using system 100 correctly. As such, display 126 may be considered a display of a graphical user interface (GUI) system. Because operating console 116 (including processor 120, storage medium 118, and communication module 122), spatial-data acquisition device (e.g., camera 124), and the various navigation devices described herein (i.e., 112, 114, 132, and 134) function together to determine the instructions, each of these components may also be considered part of the GUI system such that this GUI system comprises a subsystem of robotic surgical system 100.

FIGS. 2-6 reflect various screens that may be shown on display 126 of the GUI system, each reflecting graphical representations of instructions for using robotic surgical system 100. The instructions are determined by processor 120 based on inputs received from the spatial-data acquisition device (e.g., camera 124). The graphical representations of instructions are then further determined or selected from storage medium 118 by processor 120 and provided to display 126 such that display 126 may show the graphical representations of instructions to the surgeon.

Figure 2:
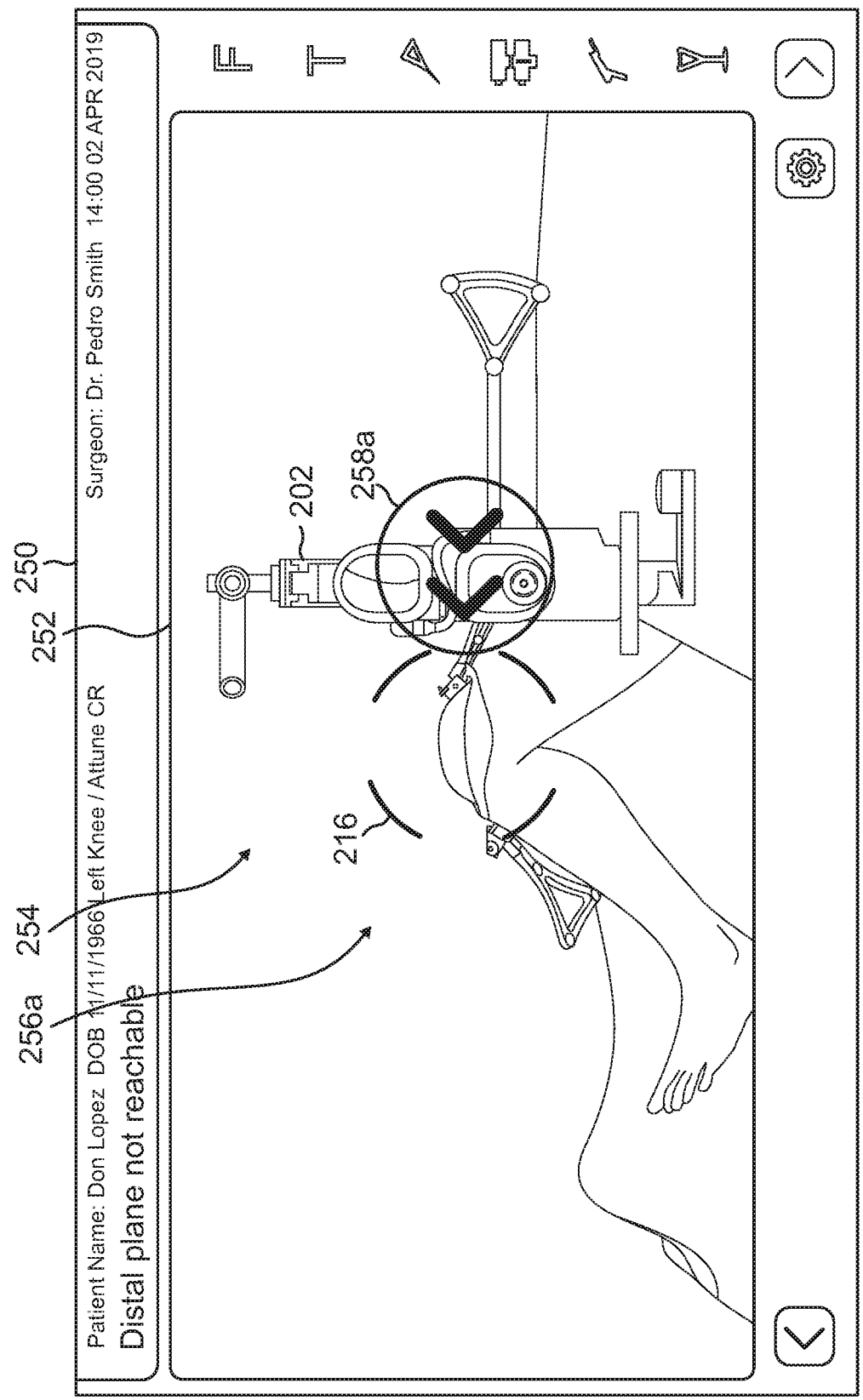
FIG. 2 depicts a first screen of the GUI system that may be shown on the display.
Figure 3:
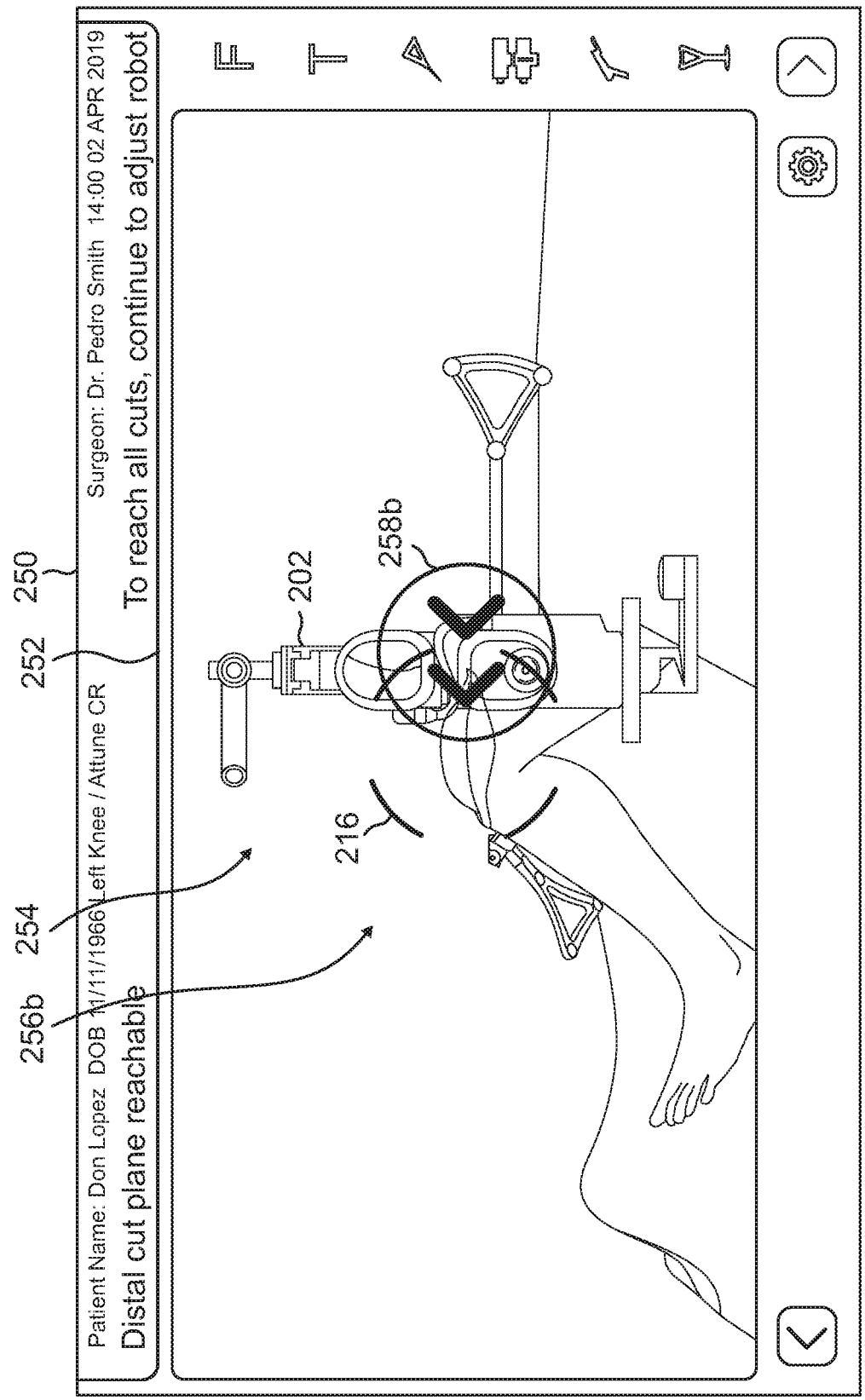
FIG. 3 depicts a second screen of the GUI system that may be shown on the display.
Figure 4:
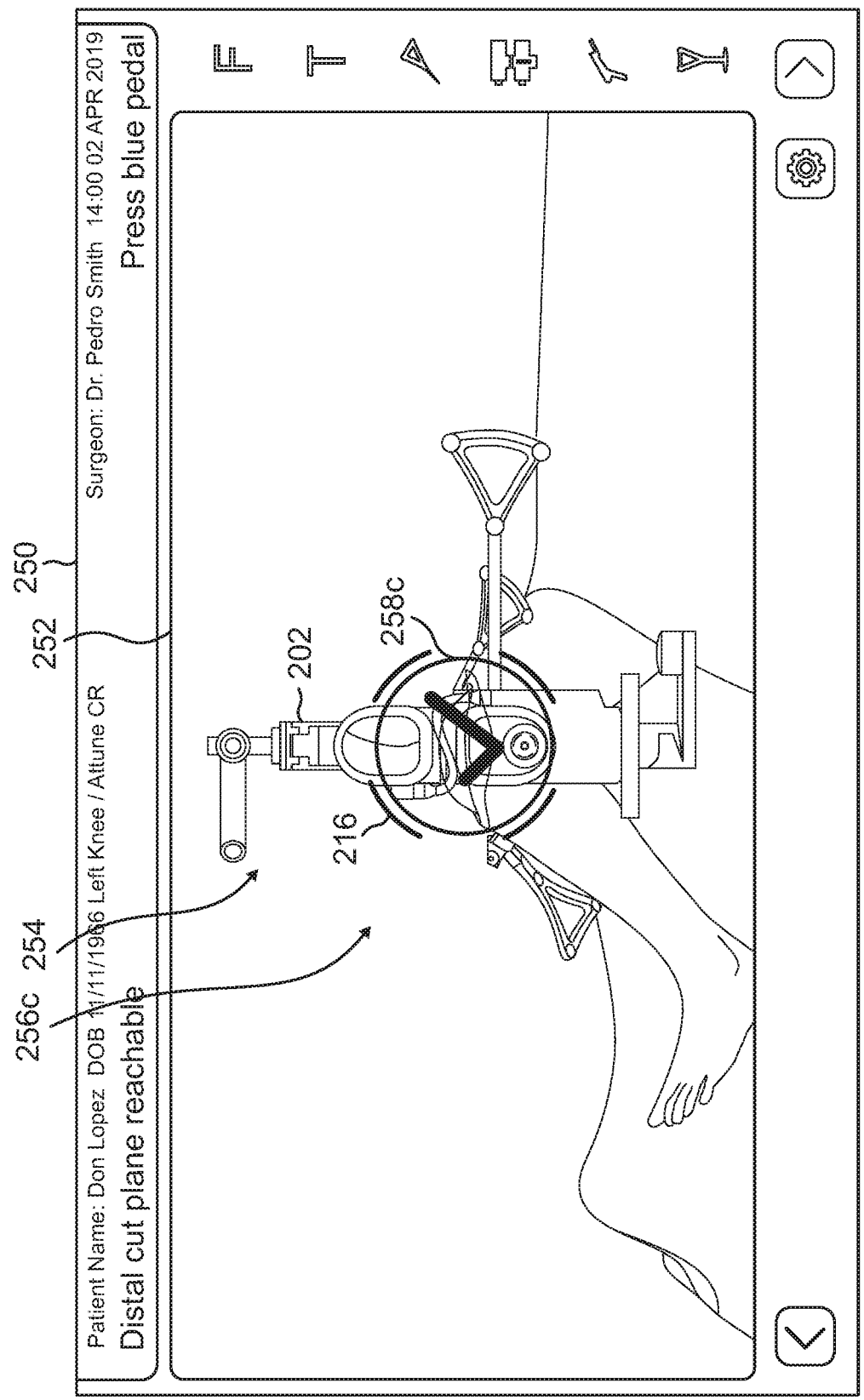
FIG. 4 depicts a third screen of the GUI system that may be shown on the display.

The first exemplary technique described herein involves using robotic surgical system 100 to assist surgeon 10 in positioning robotic surgical apparatus 102 at an anatomical target from which it may subsequently assist in performing steps of a surgical procedure, such as steps that include resecting bone. It is presumed that positioning robotic surgical apparatus at a single anatomical target from which the end effector can accomplish all of the steps (e.g., bone resections) it will perform during the surgery is preferred to an alternative whereby the robotic surgical apparatus must be moved during the surgery. FIGS. 2-4 each reflect screens that may be provided on display 126 that include graphical representations of instructions for positioning robotic surgical apparatus 102, and thus also robot body 104 and end effector 110. Specifically FIGS. 2-4 reflect screens that may be shown on display 126 that include graphical representations of instructions comprising a set of indications for positioning the robotic surgical apparatus at an anatomical target.

FIGS. 2-4 each reflect a screen 250 of display 126 (FIG. 1). A sector 252 of screen 250 shows graphical representations of instructions 254, which in this example comprises a set of indications for positioning the robotic surgical apparatus 102 at an anatomical target, such as knee 16. The representation of robotic surgical apparatus 102 on screen 250 is labeled as apparatus 202, and the anatomical target, reflected as four chords of a circle about a representation of knee 16, also referred to herein as a target indication, is labeled as 216. As such, in the example of FIGS. 2-4, the set of indications comprises various instruction images, which are the instruction images reflected in sector 252. In FIG. 2, sector 252 comprises first instruction image 256a. In FIG. 3, sector 252 comprises second instruction image 256b. In FIG. 4, sector 252 comprises third instruction image 256c.

First instruction image 256a reflects robot representation 202 positioned at a first location. First instruction image 256a also reflects a first directional indication 258a of a direction from the first location toward anatomical target 216. Second instruction image 256b reflects robot representation 202 positioned at a second location that is closer to anatomical target 216 than the first location of instruction image 256a. Second instruction image 256b also reflects a second directional indication 258b of a direction from the second location toward anatomical target 216. Third instruction image 256c reflects robot representation 202 positioned at anatomical target 216. Third instruction image 256c also reflects a confirmation indication 258c that robot representation 202 is positioned at anatomical target 216. Accordingly, instruction images 256a, 256b, and 256c may be reflected in a sequential order in sector 252 of screen 250, and processor 120 may be configured to provide them to display 126 as such.

Directional indications 258a and 258b may be overlaid on representation 202 of apparatus 102 to show the surgeon the direction in which apparatus 102 should be moved. Although it may be obvious in which direction to move apparatus 102 when the distance between apparatus 102 and the anatomical target is great, such indications have been found to be helpful for facilitating precise and correct placement of apparatus 102 at anatomical target 216 when this distance is small.

The second exemplary technique described herein involves using robotic surgical system 100 to assist surgeon 10 in confirming correctness of reference data that system 100 uses to control robotic surgical apparatus 102 in cutting bone. In other words, robotic surgical system 100 may also be used to practice the sage advice of measuring twice and cutting once.

Figure 5:
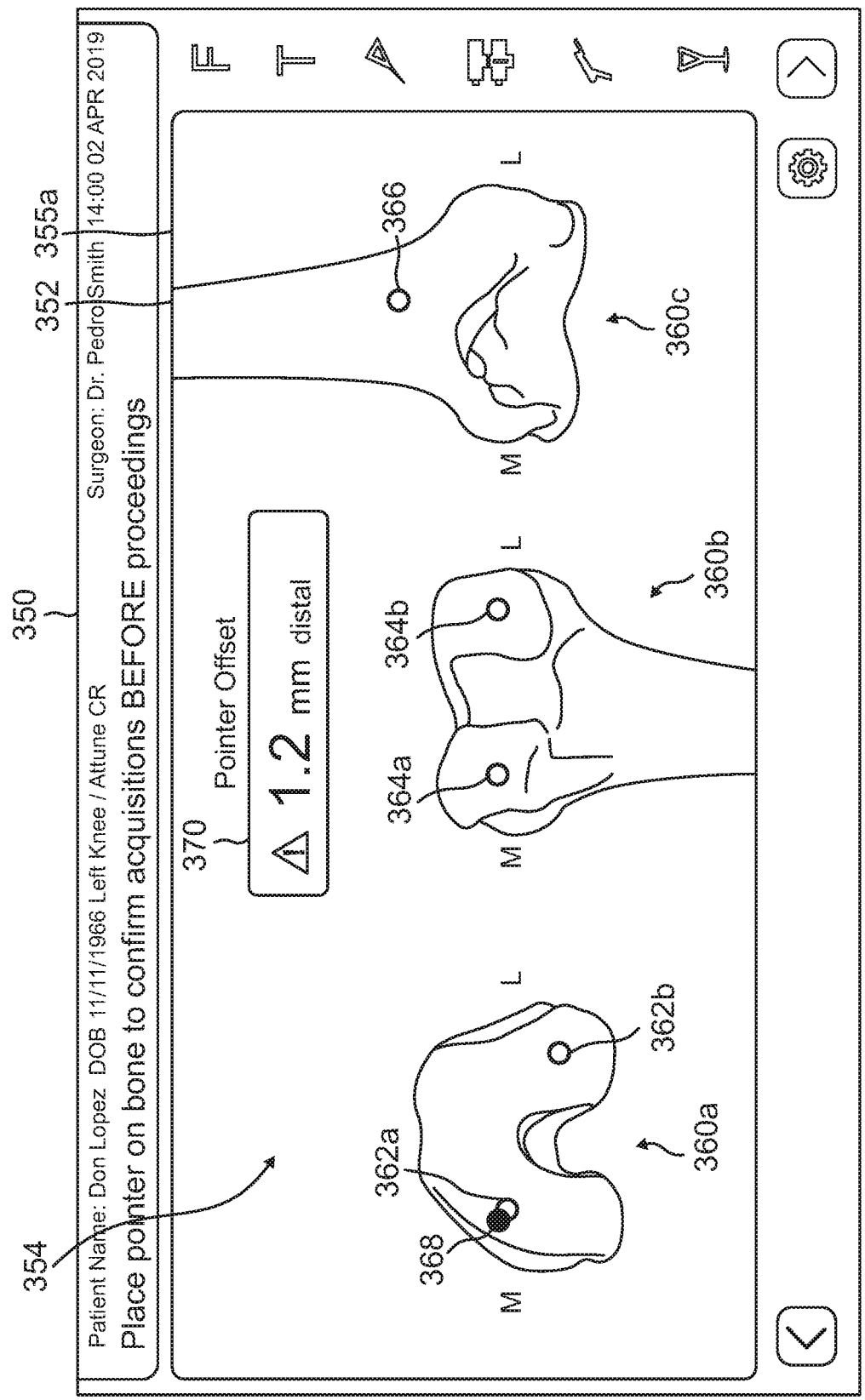
FIG. 5 depicts a fourth screen of the GUI system that may be shown on the display.
Figure 6:
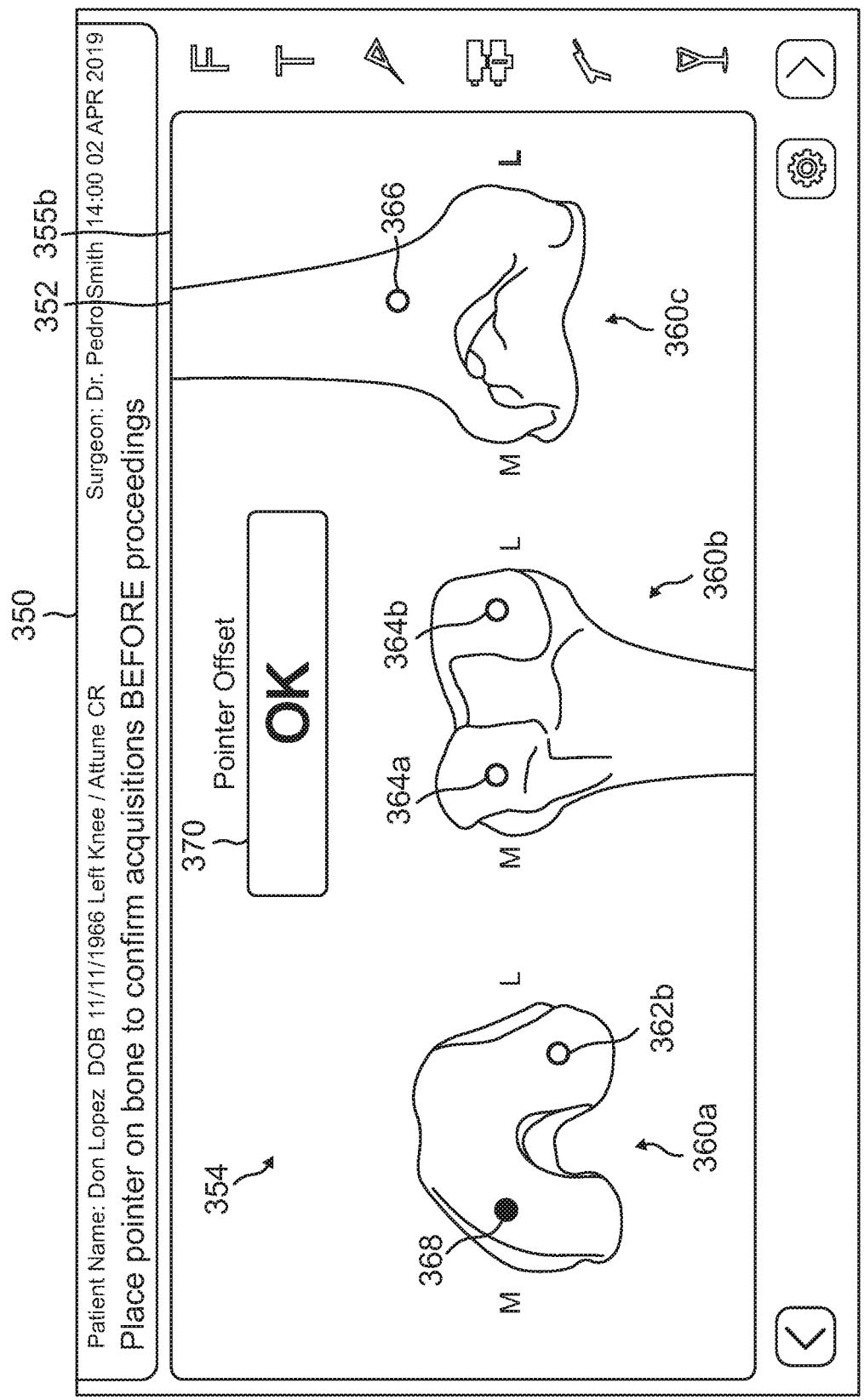
FIG. 6 depicts a fifth screen of the GUI system that may be shown on the display.

FIGS. 5-6 each reflect a screen 350 of display 126 (FIG. 1). A sector 352 of screen 350 shows graphical representations of instructions 354, which in this example comprises a set of indications for confirming a reference surface location of an anatomical structure, e.g., a proximal portion of a tibia or a distal portion of a femur. In the present example, the set of indications are reflected on a review image 355a, which fills sector 352, and the anatomical structure is the distal portion of the femur, of which three different views are provided in sector 352. First view 360a of the distal portion of the femur is a view along the proximal-distal axis from a point distal of the femur. Second view 360b of the distal portion of the femur is a view along the posterior-anterior axis from a point posterior of the femur. Third view 360c of the femur is a view along the posterior anterior axis from a point anterior of the femur. Accordingly, views 360a-c comprise two-dimensional images of the femur.

Various reference points are reflected on each view of the distal portion of the femur 360a, 360b, and 360c. The reference points 362a, 362b, 364a, 364b, and 366 represent reference surface locations on the femur that the surgeon, with the assistance of system 100, previously determined were the maximal surface locations along an anatomical direction. That is, reference points 362a and 362b were predetermined to be the most distal points on each condyle of the femur along the distal-proximal axis, reference points 364a and 364b were predetermined to be the most posterior points on each condyle of the femur along the anterior-posterior axis, and reference point 366 was predetermined to be the most anterior point along the anterior-posterior axis.

A moveable point 368 is also reflected in sector 352. Moveable point 368 represents the tip of pointer 136 of data acquisition device 134. As the surgeon moves the tip of pointer 136 over the surface of the distal portion of the femur, point 368 appears at a corresponding location on one of views 360a-c.

Also provided in sector 352 is a message box 370, which provides a pointer offset distance, i.e., a distance between the tip of the pointer of the data acquisition device 136 and the reference surface location closest thereto. Accordingly, in the example of sector 352 of FIG. 5, the distance in message box 370 is the distance between the tip of the pointer of the data acquisition device 136 and the previously determined most distal point on the medial condyle, represented by reference point 362a of view 360a. Preferably, the distance provided is a projection of the three-dimensional distance between these two points onto the anatomical axis about which each view 360a-360c are taken. As such, the distance provided in message box 370 of FIG. 5, i.e., 1.2 mm, is a distance along the distal-proximal axis. Thus, in FIG. 5, the message box indicates that the tip of pointer of the data acquisition device 136 is touching a surface location on the femur that is 1.2 mm more distal than reference point 360a, which had been previously determined to be the distal most point. Accordingly, upon seeing this indication, the surgeon may contemplate whether reference point 360a may not have been correctly acquired such that it should perhaps be re-acquired.

FIG. 6 is similar to FIG. 5 except that review image 355b includes moveable point 368 directly over reference point 362a such that reference point 362a is hidden under point 368. Correspondingly, message box 370 does not display a distance. Instead, it displays an indication that the distance between the tip of pointer of the data acquisition device 136 and the previously determined most distal point on the medial condyle is zero. That is, there is agreement between the reference data previously acquired and the current measurement. As such, the message in box 370 may read, "OK."

Figure 7:
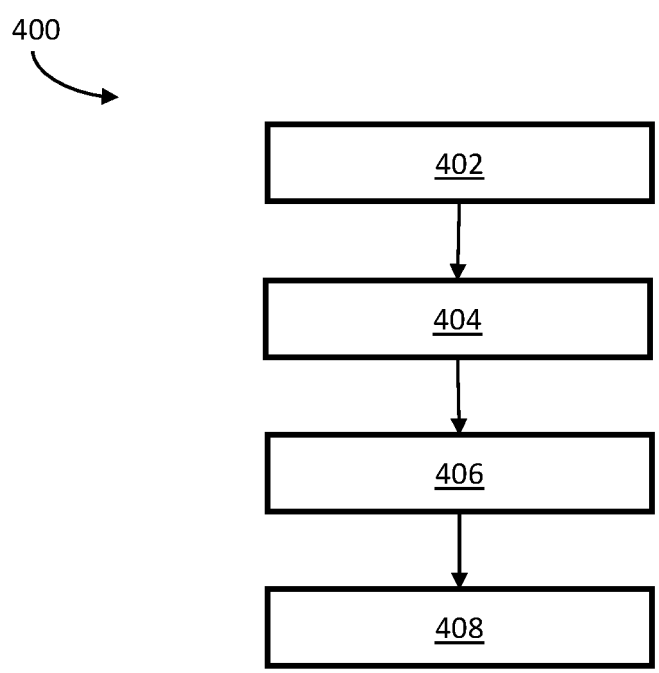
FIG. 7 depicts a flow chart for a method of using the robotic surgical system to position the robotic surgical apparatus.

By virtue of the embodiments illustrated and described herein, Applicant has devised methods and variations thereof for using robotic surgical system 100 described above. FIG. 7 reflects a flow chart corresponding to a method 400 for using robotic surgical system 100 to position robotic surgical apparatus 102. At step 402, first instruction image 256a may be displayed on display 126. At step 404, the robotic surgical apparatus may be moved from a first location to a second location that is closer to an anatomical target than the first location. At step 406, the display may be changed to show a second instruction image 256b. At step 406, the robotic surgical apparatus may be moved from the second location to the anatomical target. At step 408, the display may be changed to show a third instruction image 256c.

Step 402 may further comprise a step of generating first spatial data. For example, step 402 may comprise capturing, with camera 124, a first location image of robotic surgical apparatus 102. Step 402 may further comprise a step of sending the first location image to processor 120. Alternatively or additionally, step 402 may comprise generating a magnetic field to induce an electric signal in any three-coil sets in at least one of navigation devices 114 and 132, and then providing these signals to the processor. Step 402 may further comprise determining, with the processor, the first instruction image from the first spatial data, e.g., by calculating a direction from the first location toward the anatomical target. Step 402 may further comprise providing the first instruction image to the display.

Step 406 may further comprise a step of generating second spatial data. For example step 406 may comprise capturing, with camera 124, a second location image of robotic surgical apparatus 102. Step 406 may further comprise sending the second location image to processor 120. Alternatively or additionally, step 406 may comprise generating a magnetic field to induce an electric signal in any three-coil sets in at least one of navigation devices 114 and 132, and then providing these signals to the processor. Step 406 may further comprise determining, with the processor, the second instruction image from the second spatial data, e.g., by calculating a direction from the second location to the anatomical target. Step 406 may further comprise providing the second instruction image to the display.

Step 408 may further comprise a step of generating third spatial data. For example, step 408 may comprise capturing, with camera 124, a third location image of the robotic surgical apparatus with the camera. Alternatively or additionally, step 406 may comprise generating a magnetic field to induce an electric signal in any three-coil sets in at least one of navigation devices 114 and 132, and then providing these signals to the processor. Step 408 may further comprise sending the third spatial data to the processor. Step 408 may further comprise determining, with the processor, that the anatomical target comprises the third location. Step 408 may further comprise providing the third instruction image to the display.

Figure 8:
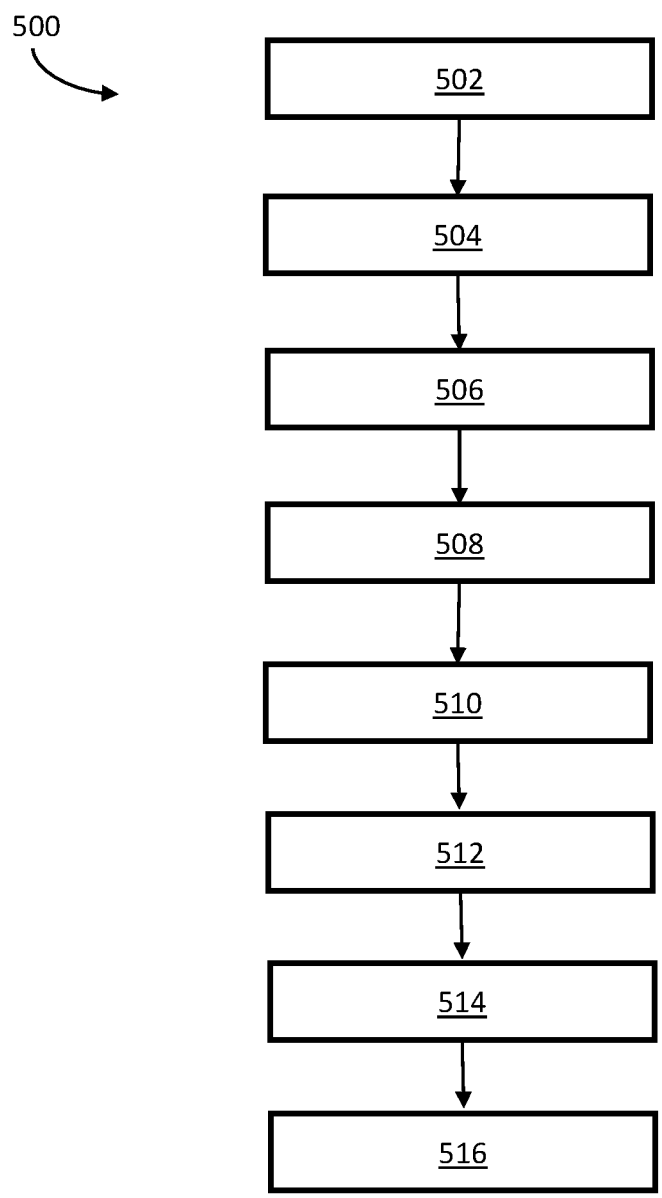
FIG. 8 depicts a flow chart for a method of using the robotic surgical system to confirm predetermined reference data.

FIG. 8 reflects a flow chart corresponding to a method 500 for using robotic surgical system 100 to position robotic surgical apparatus 102. At step 502, the tip of data acquisition device 134 may be brought into contact with a first surface location on an anatomical structure, e.g., a distal portion of a femur. At step 504, review image 355a, which includes moveable point 368 reflected at a first position on the image of the anatomical structure corresponding to the first surface location (e.g., a location removed from the reference surface location), may be displayed on display 126. At step 506, a first review distance is calculated between the reference surface location and the tip of the data acquisition device at the first surface location. At step 508, a first message indicating the first review distance may be displayed in a message box. At step 510, the tip of the data acquisition device may be moved to a second surface location on the anatomical structure such that the tip may contact the second surface location. At step 512, the moveable point may be moved to a second position on the review image corresponding to the second surface location. At step 514, a second review distance between the reference surface location and the tip of the data acquisition device at the second surface location may be calculated by the processor. At step 516, a second message may be displayed in the message box indicating the second review distance.

Step 504 may further comprise a step of generating first data-review spatial data. For example, step 504 may comprise capturing, with camera 124, a first data-review image reflecting the tip of data acquisition device contacting the anatomical structure at the first surface location. Step 504 may further comprise sending the first data-review image to the processor. Alternatively or additionally, step 504 may comprise generating a magnetic field to induce an electric signal in any three-coil sets in at least pointer navigation device 134, and then providing these signals to the processor. Step 504 may further comprise determining, with the processor, the first position of the moveable point on the review image.

Step 512 may further comprise may further comprise a step of generating second data-review spatial data. For example, step 512 may comprise capturing, with camera 124, a second data-review image reflecting the tip of the data acquisition device contacting the anatomical structure at the second surface location. Step 512 may further comprise sending the second data-review image to the processor. Alternatively or additionally, step 512 may comprise generating a magnetic field to induce an electric signal in any three-coil sets in at least pointer navigation device 134, and then providing these signals to the processor. Step 512 may further comprise determining, with the processor, the second position of the moveable point on the review image.

Various aspects of the subject matter according to the present disclosure include, but are not limited to, the aspects listed in the following numbered clauses.

1. A robotic surgical system comprising;
   a robotic surgical apparatus; and
   a graphical user interface (GUI) system, comprising:
     a camera, a display, a data acquisition device, and an operating console including a non-transitory storage medium and a processor,
     in which the robotic surgical apparatus, the camera, the display, and the non-transitory storage medium are connected to the processor; and
     in which the processor is configured to:
       receive as inputs images from the camera, and
       provide as outputs to the display graphical representations of instructions.
2. The robotic surgical system of clause 1, in which the graphical representations of instructions comprise a set of indications for positioning the robotic surgical apparatus at an anatomical target.
3. The robotic surgical system of clause 2, in which the set of indications for positioning the robotic surgical apparatus at an anatomical target comprises a first instruction image reflecting the robotic surgical apparatus positioned at a first location, a second instruction image reflecting the robotic surgical apparatus positioned at a second location that is closer to the anatomical target than the first location, and a third instruction image reflecting the robotic surgical apparatus at the anatomical target.
4. The robotic surgical system of clause 3, in which the first instruction image includes a first directional indication of a direction from the first location toward the anatomical target.
5. The robotic surgical system of clause 4, in which the second instruction image includes a second directional indication of a direction from the second location toward the anatomical target.
6. The robotic surgical system of clause 5, in which the third instruction image includes a confirmation indication that the robotic surgical apparatus is positioned at the anatomical target.
7. The robotic surgical system of clause 6, in which the first instruction image, the second instruction image, or both, include a target indication disposed about the anatomical target.
8. The robotic surgical system of clause 7, in which the processor is further configured to sequentially provide as outputs to the display the first instruction image, the second instruction image, and the third instruction image.
9. The robotic surgical system of any of the preceding clauses, in which the graphical representations of instructions comprise a set of indications for confirming a reference surface location of an anatomical structure.
10. The robotic surgical system of clause 9, in which the set of indications for confirming the reference surface location of an anatomical structure comprises:
    a review image reflecting the anatomical structure;
    a reference point on the review image representing the reference surface location on the anatomical structure;
    a moveable point on the review image representing a tip of the data acquisition device; and
    a message box for indicating a distance between the reference surface location and the location of the tip of the data acquisition device.
11. The robotic surgical system of clause 10, in which the reference surface location comprises a maximal surface location along an anatomical direction.
12. The robotic surgical system of clause 11, in which the maximal surface location along an anatomical direction comprises a most-distal surface location.
13. The robotic surgical system of any of clauses 10-12, in which the distance between the reference surface location and the location of the tip of the data acquisition device comprises a component along an anatomical axis.
14. The robotic surgical system of clause 13, in which the anatomical axis comprises the distal-proximal axis.
15 The robotic surgical system of clause 10-14, in which the review image comprises a two-dimensional image of the anatomical structure.
16. The robotic surgical system of any of the preceding clauses, in which the data acquisition device comprises a navigation device and a pointer comprising the tip of the data acquisition device.
17. A method of using the robotic surgical system of any of the preceding clauses, comprising:
    displaying on the display the first instruction image;
    moving the robotic surgical apparatus from the first location to the second location;
    changing the display from the first instruction image to the second instruction image;
    moving the robotic surgical apparatus from the second location to the anatomical target; and
    changing the display from the second instruction image to the third instruction image.
18. The method of clause 17, in which the step of displaying on the display the first instruction image comprises:
    capturing, with the camera, a first location image of the robotic surgical apparatus;
    sending the first location image to the processor;
    with the processor, determining the first instruction image from the first location image; and
    providing the first instruction image to the display.
19. The method of clause 18, in which the step of determining the first instruction image from the first location image comprises calculating the direction from the first location toward the anatomical target.
20. The method of any of clauses 17-19, in which the step of changing the display from the first instruction image to the second instruction image comprises:

capturing a second location image of the robotic surgical apparatus with the camera;
sending the second location image to the processor;
with the processor, determining the second instruction image from the second location image; and
providing the second instruction image to the display.
21. The method of clause 20, in which the step of determining the second instruction image from the second location image further comprises calculating the direction from the second location to the anatomical target.
22. The method of any of clauses 17-21, in which the step of changing the display from the second instruction image to the third instruction image comprises:
capturing a third location image of the robotic surgical apparatus with the camera;
sending the third location image to the processor;
with the processor, determining that the anatomical target comprises the third location; and
providing the third instruction image to the display.
23. A method of using the robotic surgical system of any of clauses 1-16, comprising,
contacting the tip of the data acquisition device to a first surface location on the anatomical structure; and
displaying on the display the review image with the moveable point reflected at a first position on the image of the anatomical structure corresponding to the first surface location;
calculating a first review distance between the reference surface location and the tip of the data acquisition device at the first surface location; and
displaying on the display a first message in the message box indicating the first review distance.
24. The method of clause 23, in which the tip of the data acquisition device does not contact the reference surface location.
25. The method of clause 23, further comprising:
moving the tip of the data acquisition device to a second surface location on the anatomical structure;
contacting the tip of the data acquisition device to the second surface location;
moving the moveable point to a second position on the review image corresponding to the second surface location;
calculating a second review distance between the reference surface location and the tip of the data acquisition device at the second surface location; and
displaying on the display a second message in the message box indicating the second review distance.
26. The method of any of clauses 23-25, in which the step of displaying on the display the review image with the moveable point reflected at the first position comprises:
capturing, with the camera, a first data-review image reflecting the data acquisition device and the tip thereof contacting the anatomical structure at the first surface location;
sending the first data-review image to the processor; and
with the processor, determining the first position of the moveable point on the review image.
27. The method of clauses 25 or 26, in which the step of moving the moveable point to a second position on the review image comprises:
capturing, with the camera, a second data-review image reflecting the data acquisition device and the tip thereof contacting the anatomical structure at the second surface location;
sending the second data-review image to the processor; and
with the processor, determining the second position of the moveable point on the review image.
28. A robotic surgical system, comprising;
a robotic surgical apparatus; and
a graphical user interface (GUI) system, comprising:
a spatial-data acquisition device, a display, and an operating console including a non-transitory storage medium and a processor,
in which the robotic surgical apparatus, the spatial-data acquisition device, the display, and the non-transitory storage medium are connected to the processor, and
in which the processor is configured to:
receive as inputs spatial data from the spatial-data acquisition device, and
provide as outputs to the display a set of indications for positioning the robotic surgical apparatus at the anatomical target.
29. The robotic surgical system of clause 28, in which the set of indications for positioning the robotic surgical apparatus at an anatomical target comprises a first instruction image reflecting the robotic surgical apparatus positioned at a first location, a second instruction image reflecting the robotic surgical apparatus positioned at a second location that is closer to the anatomical target than the first location, and a third instruction image reflecting the robotic surgical apparatus at the anatomical target.
30. The robotic surgical system of clause 29, in which the first instruction image includes a first directional indication of a direction from the first location toward the anatomical target.
31. The robotic surgical system of clause 30, in which the second instruction image includes a second directional indication of a direction from the second location toward the anatomical target.
32. The robotic surgical system of clause 31, in which the third instruction image includes a confirmation indication that the robotic surgical apparatus is positioned at the anatomical target.
33. The robotic surgical system of clause 32, in which the first instruction image, the second instruction image, or both, include a target indication disposed about the anatomical target.
34. The robotic surgical system of clause 33, in which the processor is further configured to sequentially provide as outputs to the display the first instruction image, the second instruction image, and the third instruction image.
35 The robotic surgical system of clause 33, in which the spatial-data acquisition device comprises a thermographic camera and the spatial data comprise an infrared image.
36. A robotic surgical system, comprising:
a robotic surgical apparatus; and
a graphical user interface (GUI) system, comprising:
a spatial-data acquisition device, a display, a data acquisition device, and an operating console including a non-transitory storage medium and a processor,
in which the robotic surgical apparatus, the spatial-data acquisition device, the display, and the non-transitory storage medium are connected to the processor; and
in which the processor is configured to:

receive as inputs spatial data from the spatial-data acquisition device, and provide as outputs to the display a set of indications for confirming the reference surface location of the anatomical structure.

37. The robotic surgical system of clause 36, in which the set of indications for confirming the reference surface location of an anatomical structure comprises:
a review image reflecting the anatomical structure;
a reference point on the review image representing the reference surface location on the anatomical structure;
a moveable point on the review image representing a tip of the data acquisition device; and
a message box for indicating a distance between the reference surface location and the location of the tip of the data acquisition device.

38. The robotic surgical system of clause 37, in which the reference surface location comprises a maximal surface location along an anatomical direction.

39. The robotic surgical system of clause 38, in which the maximal surface location along an anatomical direction comprises a most-distal surface location.

40. The robotic surgical system of clause 39, in which the distance between the reference surface location and the location of the tip of the data acquisition device comprises a component along an anatomical axis.

41. The robotic surgical system of clause 40, in which the anatomical axis comprises the distal-proximal axis.

42 The robotic surgical system of clause 41, in which the review image comprises a two-dimensional image of the anatomical structure.

43. The robotic surgical system of clause 42, in which the data acquisition device comprises a navigation device and a pointer comprising the tip of the data acquisition device.

44. The robotic surgical system of clause 42, in which the spatial-data acquisition device comprises a thermographic camera and the spatial data comprise an infrared image.

45. A method of using a robotic surgical system comprising a processor and a robotic surgical apparatus to position the robotic surgical apparatus, the method comprising:
displaying on a display a first instruction image;
moving the robotic surgical apparatus from a first location to a second location;
changing the display from the first instruction image to a second instruction image;
moving the robotic surgical apparatus from the second location to an anatomical target; and
changing the display from the second instruction image to a third instruction image.

46. The method of clause 45, in which the step of displaying on the display the first instruction image comprises:
collecting, with a spatial-data acquisition device, first spatial data of the robotic surgical apparatus;
sending the first spatial data to the processor;
with the processor, determining the first instruction image from the first spatial data; and
providing the first instruction image to the display.

47. The method of clause 46, in which the step of determining the first instruction image from the first spatial data comprises calculating a direction from the first location toward the anatomical target.

48 The method of clause 47, in which the step of changing the display from the first instruction image to the second instruction image comprises:
collecting, with the spatial-data acquisition device, second spatial data of the robotic surgical apparatus;
sending the second spatial data to the processor;
with the processor, determining the second instruction image from the second spatial data; and
providing the second instruction image to the display.

49. The method of clause 48, in which the step of determining the second instruction image from the second spatial data further comprises calculating a direction from the second location to the anatomical target.

50. The method of clause 49, in which the step of changing the display from the second instruction image to the third instruction image comprises:
collecting, with the spatial-data acquisition device, third spatial data of the robotic surgical apparatus;
sending the third spatial data to the processor;
with the processor, determining that the anatomical target comprises the third location; and
providing the third instruction image to the display.

51. A method of using a robotic surgical system comprising a processor to confirm predetermined reference data, the method comprising:
contacting a tip of a data acquisition device to a first surface location on an anatomical structure;
displaying on a display a review image with a moveable point reflected at a first position on the anatomical structure corresponding to the first surface location;
calculating a first review distance between the reference surface location and the tip of the data acquisition device at the first surface location; and
displaying on the display a first message indicating the first review distance.

52. The method of clause 51, in which the tip of the data acquisition device does not contact the reference surface location.

53. The method of clause 51, further comprising:
moving the tip of the data acquisition device to a second surface location on the anatomical structure;
contacting the tip of the data acquisition device to the second surface location;
moving the moveable point to a second position on the review image corresponding to the second surface location;
calculating a second review distance between the reference surface location and the tip of the data acquisition device at the second surface location; and
displaying on the display a second message indicating the second review distance.

54. The method of clause 53, in which the step of displaying on the display the review image with the moveable point reflected at the first position comprises:
collecting, with a spatial-data acquisition device, first data-review spatial data of the data acquisition device when the tip thereof is contacting the anatomical structure at the first surface location;
sending the first data-review spatial data to the processor; and
with the processor, determining the first position of the moveable point on the review image.

55. The method of clause 54, in which the step of moving the moveable point to a second position on the review image comprises:

collecting, with the spatial-data acquisition device, second data-review spatial data of the data acquisition device when the tip thereof is contacting the anatomical structure at the second surface location;

sending the second data-review spatial data to the processor; and with the processor, determining the second position of the moveable point on the review image.

56. The method of clause 55, in which the spatial-data acquisition device comprises a camera and the first data-review spatial data comprises a first data-review image captured by the camera that reflects the tip of the data acquisition device contacting the anatomical structure at the first surface location.

57. The method of clause 56, in which the second data-review spatial data comprises a second data-review image captured by the camera that reflects the tip of the data acquisition device contacting the anatomical structure at the second surface location.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

I claim:

1. A robotic surgical system, comprising:
   a robotic surgical apparatus; and
   a graphical user interface (GUI) system, comprising:
   a spatial-data acquisition device, a display, a data acquisition device, and an operating console including a non-transitory storage medium and a processor,
   in which the robotic surgical apparatus, the spatial-data acquisition device, the display, and the non-transitory storage medium are connected to the processor; and
   in which the processor is configured to:
      receive as inputs spatial data from the spatial-data acquisition device, and
      provide as outputs to the display a set of indications for confirming a previously determined maximal surface location of an anatomical structure,
   in which the set of indications for confirming the previously determined maximal surface location comprises:
      a review image reflecting the anatomical structure;
      a reference point on the review image representing the previously determined maximal surface location;
      a single tip-representation point on the review image that represents a location of a tip of the data acquisition device when the tip is being moved over a surface of the anatomical structure from a first surface location on the anatomical structure to a second surface location on the anatomical structure; and
      a message box for indicating a distance between the previously determined maximal surface location and the tip of the data acquisition device when the tip is being moved over the surface of the anatomical structure.

2. The robotic surgical system of claim 1, in which the previously determined maximal surface location comprises a previously determined maximal surface location along an anatomical direction.

3. The robotic surgical system of claim 2, in which the previously determined maximal surface location along an anatomical direction comprises a most-distal surface location.

4. The robotic surgical system of claim 3, in which the distance between the previously determined maximal surface location and the single tip-representation point comprises a component along the anatomical axis.

5. The robotic surgical system of claim 4, in which the anatomical axis comprises the distal-proximal axis.

6. The robotic surgical system of claim 5, in which the review image comprises a two-dimensional image of the anatomical structure.

7. The robotic surgical system of claim 6, in which the data acquisition device comprises a navigation device and a pointer comprising the tip of the data acquisition device.

8. The robotic surgical system of claim 6, in which the spatial-data acquisition device comprises a thermographic camera and the spatial data comprise an infrared image.

9. A method of using a robotic surgical system comprising a processor to confirm a previously determined maximal surface location of an anatomical structure along an anatomical direction, the method comprising:
   contacting a tip of a data acquisition device to a first surface location on the anatomical structure;
   displaying on a display a review image with a single tip-representation point that represents a location of the tip of the data acquisition device when the tip of the data acquisition device is moved over a surface of the anatomical structure from the first surface location on the anatomical structure to a second surface location on the anatomical structure, the single tip-representation being initially reflected at a first position on the anatomical structure corresponding to the first surface location;
   calculating a first review distance between the previously determined maximal surface location and the tip of the data acquisition device while the tip is in contact with the anatomical structure at the first surface location; and
   displaying on the display a first message indicating the first review distance.

10. The method of claim 9, in which the tip of the data acquisition device does not contact the previously determined maximal surface location.

11. The method of claim 9, further comprising:
   moving the tip of the data acquisition device to a second surface location on the anatomical structure;
   contacting the tip of the data acquisition device to the second surface location;

moving the single tip-representation point to a second position on the review image corresponding to the second surface location;

calculating a second review distance between the previously determined maximal surface location and the tip of the data acquisition device while the tip is in contact with the anatomical structure at the second surface location; and displaying on the display a second message indicating the second review distance.

12. The method of claim 11, in which the step of displaying on the display the review image with the single tip-representation point reflected at the first position comprises:

collecting, with a spatial-data acquisition device, first data-review spatial data of the data acquisition device when the tip thereof is contacting the anatomical structure at the first surface location;

sending the first data-review spatial data to the processor; and with the processor, determining the first position of the single tip-representation point on the review image.

13. The method of claim 12, in which the step of moving the single tip-representation point to a second position on the review image comprises:

collecting, with the spatial-data acquisition device, second data-review spatial data of the data acquisition device when the tip thereof is contacting the anatomical structure at the second surface location;

sending the second data-review spatial data to the processor; and with the processor, determining the second position of the single tip-representation point on the review image.

14. The method of claim 13, in which the spatial-data acquisition device comprises a camera and the first data-review spatial data comprises a first data-review image captured by the camera that reflects the tip of the data acquisition device contacting the anatomical structure at the first surface location.

15. The method of claim 14, in which the second data-review spatial data comprises a second data-review image captured by the camera that reflects the tip of the data acquisition device contacting the anatomical structure at the second surface location.

* * * * *